(12) United States Patent
Hsu et al.

(10) Patent No.: US 12,742,729 B2
(45) Date of Patent: Sep. 22, 2026

(54) INTEGRATION OF FLUID ANALYZER MODULE MEASUREMENTS FOR QUALITY CONTROL OF FLUID SAMPLING AND PROCESSES FOR USING SAME

(71) Applicant: Schlumberger Technology Corporation, Sugar Land, TX (US)

(72) Inventors: Kai Hsu, Sugar Land, TX (US); Hua Chen, Sugar Land, TX (US); Richard Jackson, Houston, TX (US); Evgeniya Deger, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 150 days.

(21) Appl. No.: 18/898,774

(22) Filed: Sep. 27, 2024

(65) Prior Publication Data

US 2025/0110050 A1 Apr. 3, 2025

Related U.S. Application Data

(60) Provisional application No. 63/586,731, filed on Sep. 29, 2023.

(51) Int. Cl.
*G01N 21/3577* (2014.01)
*G01N 1/14* (2006.01)
(Continued)

(52) U.S. Cl.
CPC ........... *G01N 21/3577* (2013.01); *G01N 1/14* (2013.01); *G01N 33/2823* (2013.01); *G01N 35/00623* (2013.01); *G01N 2021/3595* (2013.01)

(58) Field of Classification Search
CPC ...... G01N 1/14; G01N 21/35; G01N 21/3577; G01N 33/28; G01N 33/2823; G01N 35/00; G01N 35/00623; G01N 2021/3595
See application file for complete search history.

(56) References Cited

U.S. PATENT DOCUMENTS

2004/0233446 A1 11/2004 Dong
2021/0388721 A1 12/2021 Hsu

OTHER PUBLICATIONS

Campo, C. D. et al., Advances in Fluid Sampling With Formation Testers for Offshore Exploration, The Offshore Technology Conference, OTC-18201-MS, May 1, 2006, pp. 1-10.

(Continued)

*Primary Examiner* — Jurie Yun
(74) *Attorney, Agent, or Firm* — Jeffrey D. Frantz

(57) ABSTRACT

In some embodiments, a process can include obtaining a first formation fluid sample using a sample-line of a focused fluid sampling system and obtaining a second formation fluid sample using a guard-line of the focused fluid sampling system. The process can also include measuring a first optical density spectrum of the first formation fluid sample and measuring a second optical density spectrum of the second formation fluid sample. The process can also include decolorizing the first and second optical density spectrums to produce a decolorized first spectrum and a decolorized second spectrum, respectively. The process can also include normalizing the first and second decolorized spectrums to provide a first normalized spectrum and a second normalized spectrum. The process can also include determining a difference between the first and the second normalized spectrums to provide a sampling difference and adjusting a fluid sampling operation based on the sampling difference.

16 Claims, 9 Drawing Sheets

(51) Int. Cl.
*G01N 33/28* (2006.01)
*G01N 35/00* (2006.01)
*G01N 21/35* (2014.01)

(56) References Cited

OTHER PUBLICATIONS

Kristensen, M. et al., Flow Modeling and Comparative Analysis for a New Generation of Wireline Formation Tester Modules, The SPE Latin America and Caribbean Petroleum Engineering Conference, SPE-169341-MS, May 21, 2014, pp. 1-16.
Mullins, O. C., et al., "Electronic Absorption Edge of Petroleum", Applied Spectroscopy, Sep. 1992, pp. 1405-1411, vol. 46, Issue 9.
Mullins, O. C., et al., "First Observation of the Urbach Tail in a Multicomponent Organic System", Applied Spectroscopy, Feb. 1992, pp. 354-356, vol. 46, Issue 2.
Okeefe, M. et al., Focused Sampling of Reservoir Fluids Achieves Undetectable Levels of Contamination, SPE Reservoir Evaluation Engineering, SPE-101084-PA, Apr. 24, 2008, pp. 205-218, vol. 11, Issue 2.
Weinheber, P. et al., New Formation Tester Probe Design for Low Contamination Sampling, The SPWLA 47th Annual Logging Symposium, Jun. 4, 2006, pp. 1-11.
Wikipedia.org, "Iteratively reweighted least squares", Retrieved from: https://en.wikipedia.org/wiki/Iteratively_reweighted_least_squares, Jun. 4, 2024, 3 pages.

INTEGRATION OF FLUID ANALYZER MODULE MEASUREMENTS FOR QUALITY CONTROL OF FLUID SAMPLING AND PROCESSES FOR USING SAME

CROSS-REFERENCE TO RELATED APPLICATION

This application claims priority to and the benefit of U.S. Provisional Patent Application Ser. No. 63/586,731, entitled "INTEGRATION OF FLUID ANALYZER MODULE MEASUREMENTS FOR QUALITY CONTROL OF FLUID SAMPLING AND PROCESSES FOR USING SAME," filed Sep. 29, 2023, which is hereby incorporated by reference in its entirety for all purposes.

FIELD

Embodiments described generally relate to quality control in fluid sampling. More particularly, such embodiments relate to the integration of fluid analyzer module measurements for quality control of fluid sampling and processes for using same.

BACKGROUND

Focused sampling techniques represent a breakthrough in downhole fluid sampling. Focused sampling techniques enable a downhole formation tester to obtain representative fluid samples much faster than with conventional approaches. For example, a focused sampling tool with two separate pumps to control fluid flow from the formation through the central and perimeter areas of a sampling zone can be used. The formation fluid can be pumped through the central area flow in the sample-line and through the perimeter area flow in the guard-line. The fluid cleanup process can be monitored during the sampling operation using optical spectrometers on both flowlines and the acquired optical measurements help the tool operator make control decisions, such as adjusting pump rates and filling sample bottles when an acceptable contamination level is reached.

Three dimensional (3D) radial probes can be used to further expand the operating envelope of fluid sampling. By using multiple fluid drains spaced circumferentially around the tool, the new modules can sample fluid in low mobility formations and sustain a high pressure differential. Furthermore, the latest generation of 3D radial probes can now perform focused sampling operations, where the flow rates on the sample and guard-lines are controlled by separate pumps and fluid sampling properties can be measured simultaneously across a dual flowline with a single fluid analyzer module (FISO). However, there exists no tools or processes that integrate FISO data into fluid sampling quality control.

There is a need, therefore, for processes that integrate FISO data into fluid sampling quality control.

SUMMARY

The integration of fluid analyzer module measurements for quality control of fluid sampling and processes for using same are provided. In some embodiments, the process can include obtaining a first formation fluid sample using a sample-line of a focused fluid sampling system, obtaining a second formation fluid sample using a guard-line of the focused fluid sampling system, measuring a first optical density spectrum of the first formation fluid sample obtained via the sample-line, measuring a second optical density spectrum of the second formation fluid sample obtained via the guard-line, decolorizing the first and the second optical density spectrums to produce a decolorized first spectrum and a decolorized second spectrum, respectively, normalizing the first and the second decolorized spectrums to provide a first normalized spectrum and a second normalized spectrum, determining a difference between the first and the second normalized spectrums to provide a sampling difference, and adjusting a fluid sampling operation based on the sampling difference.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments. It is contemplated that elements disclosed in one embodiment can be utilized in other embodiments without specific recitation.

DETAILED DESCRIPTION

Figure 1A:
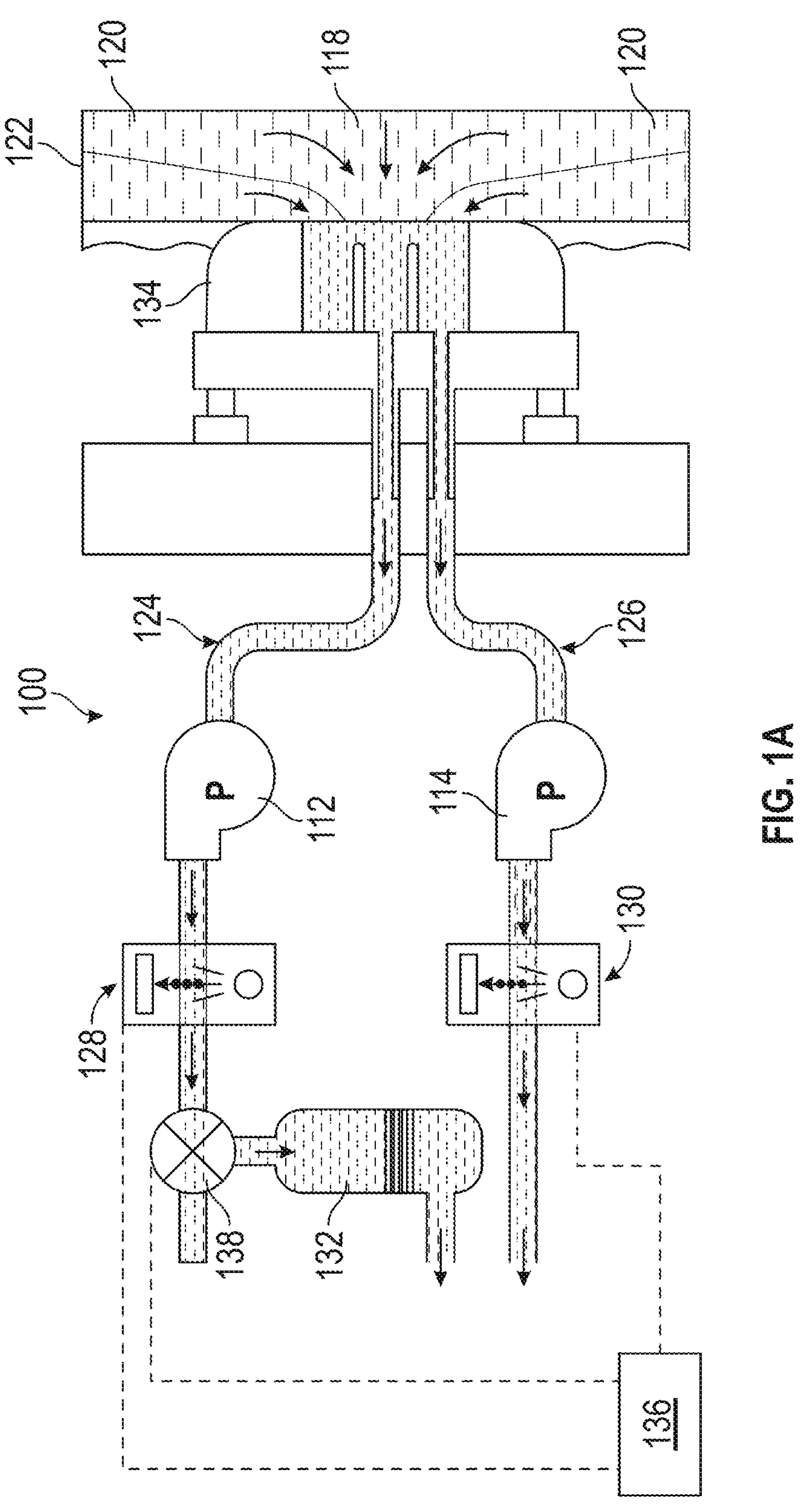
FIG. 1A depicts a schematic of an illustrative focused sampling system, according to one or more embodiments described.

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various embodiments and across the figures provided herein. This repetition is for the purpose of simplicity and clarity and does not in itself dictate a relationship between the various embodiments and/or configurations. Moreover, the exemplary embodiments presented below can be combined in any combination of ways, i.e., any element from one exemplary embodiment can be used in any other exemplary embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately," "about," "generally," and "substantially" may refer to an amount that is within less than 10% of, within less than 5% of, within less than 1% of, within less than 0.1% of, and/or within less than 0.01% of the stated amount.

Furthermore, in the following discussion and in the claims, the terms "including" and "comprising" are used in an open-ended fashion, and thus should be interpreted to mean "including, but not limited to."

The term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise. For example, embodiments using "an optical density difference" includes embodiments where one, two, or more optical density differences are used, unless specified to the contrary or the context clearly indicates that only one optical density difference is used.

Unless otherwise indicated herein, all numerical values are "about" or "approximately" the indicated value, meaning the values take into account experimental error, machine tolerances and other variations that would be expected by a person having ordinary skill in the art. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

FIG. 1A depicts a schematic of an illustrative focused sampling system 100, according to one or more embodiments. In some embodiments, the system 100 can include two separate pumps, e.g., a first pump 112 and a second pump 114, to control fluid flow from a formation in a hydrocarbon reservoir of interest through a central area 118 and a perimeter area 120 of a sampling zone 122. Fluid pumped through the central area 118 can flow into a sample-line 124 and fluid pumped through the perimeter area 120 can flow into a guard-line 126. Fluid cleanup processes can be monitored during the sampling operation using optical spectrometers on both the sample-line (e.g., a sample optical spectrometer 128) and the guard-line (e.g., a guard optical spectrometer 130). Optical measurements obtained from the optical spectrometers 128, 130 can be used by an operator to control operation of the system 100. For example, the operator may adjust pump flow rates and filling of sample bottles 132 of the system 100 when a desirable contamination level has been reached. In certain examples, the system 100 can include a 3D radial probe 134 that can improve the operating envelope of fluid sampling by using multiple fluid drains spaced circumferentially around the system 100. Accordingly, the system 100 can sample fluid in low mobility formations and sustain a high pressure differential.

In some embodiments, the system 100 can include a controller 136 that can be communicatively coupled to the sample optical spectrometer 128, the guard optical spectrometer 130, and/or a valve 138 that can be disposed along the sample-line 124. The controller 136 can receive feedback from the sample optical spectrometer 128 and/or the guard optical spectrometer 130 to perform calculations of the presently disclosed process for estimating contamination of the formation fluid. The controller 136 can utilize the estimates contamination of the formation fluid to adjust the valve 138. For example, the valve 138 can be adjusted between an open position that enables formation fluid from the sample-line 124 to enter and/or fill the sample bottle 132 and a closed position that blocks formation fluid from the sample-line 124 from entering the sample bottle 132. As such, the controller 136 can be used to determine the estimated contamination of the formation fluid and adjust the valve 138 from the closed position to the open position when the estimated level of contamination in the formation fluid falls below a threshold value that is suitable for sampling.

The system 100 can provide well-calibrated responses to fluids in dual flowlines. In other words, spectral responses of fluids in both flowlines can be identical if the same fluid is present in both flowlines. Conversely, the spectral responses of fluids in both flow lines can be different if different fluids are present in the two flow lines. For example, a difference between the spectral responses of fluids in the dual flowlines can distinguish different fluids existing in the sample-line 124 and the guard-line 126, respectively. In one or more embodiments, the system 100 can be the same or substantially the same as the focused sampling system disclosed in U.S. Patent Application Publication No. 2021/0388721.

Figure 1B:
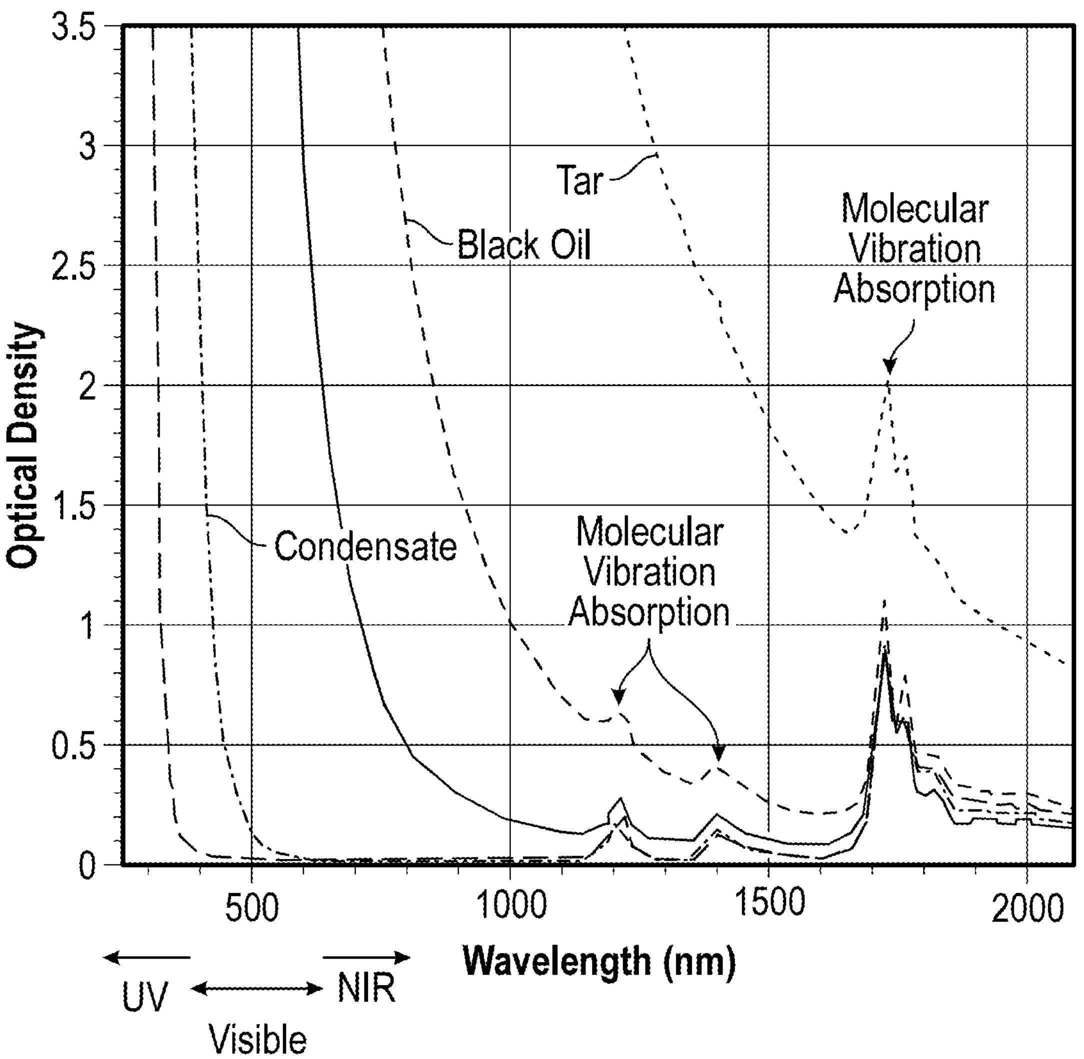
FIG. 1B depicts a graphical representation of color absorption and molecular vibration absorption of crude oils, according to one or more embodiments described.

FIG. 1B depicts a graphical representation of color absorption and molecular vibration absorption of crude oils, according to one or more embodiments. The color absorption and molecular vibration of crude oils can include regions of visible light with a wavelength of about 400-700 nm and near-infrared ("NIR") light with wavelength of about 800-2000 nm. An optical density ("OD") equal to or about 0 can be interpreted to mean that all incident light is transmitted through the fluid. An OD equal to or about 1 can be interpreted to mean that all incident light transmitted through the fluid is or is about ten times less intense than the incident light. An OD equal to or about 2 can be interpreted to mean that all incident light transmitted through the fluid is or is about one hundred times less intense than the incident light. Wavelength channels up to about 1,600 nm can be referred to as color channels and wavelength channels in the region of greater than 1,600 to about 1800 nm can be referred to as hydrocarbon channels. The color channels can be spectroscopically analyzed as color absorption. The hydrocarbon channels can be spectroscopically analyzed as gaseous absorption and dead-oil absorption. Dead-oil can be any crude oil, hydrocarbon, or other like fluid that has no or substantially no gaseous and/or volatile components within the fluid.

Figure 2A:
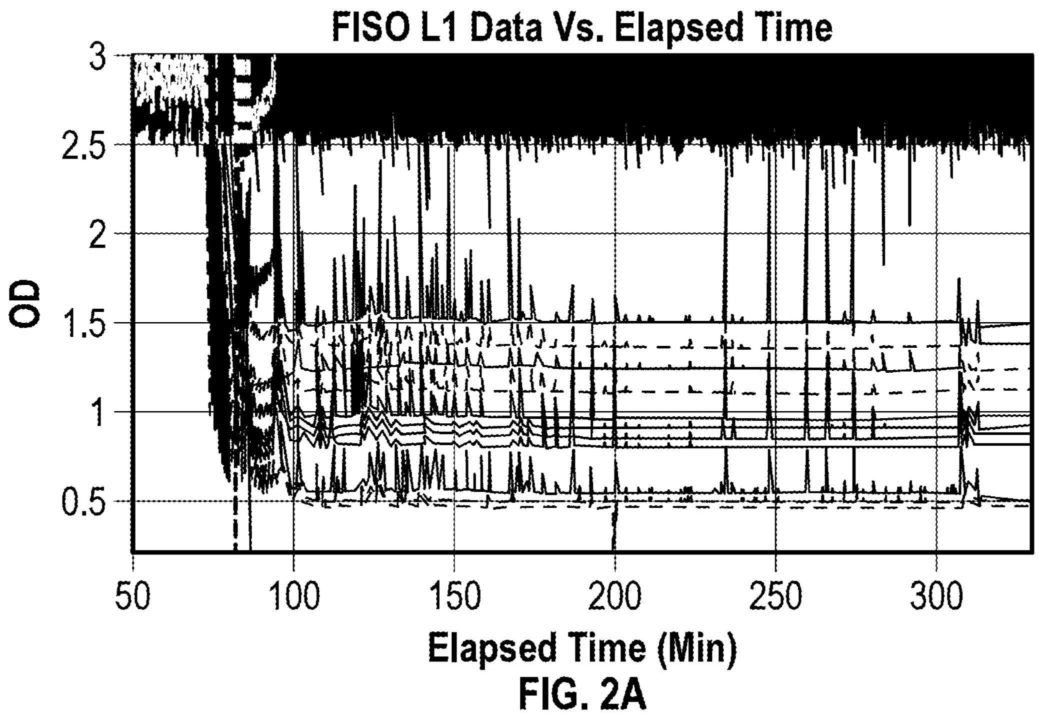
FIG. 2A depicts a graphical representation of optical density spectra of typical downhole fluids obtained via a sample-line of a focused fluid sampling system over an elapsed period of time, according to one or more embodiments described.
Figure 2B:
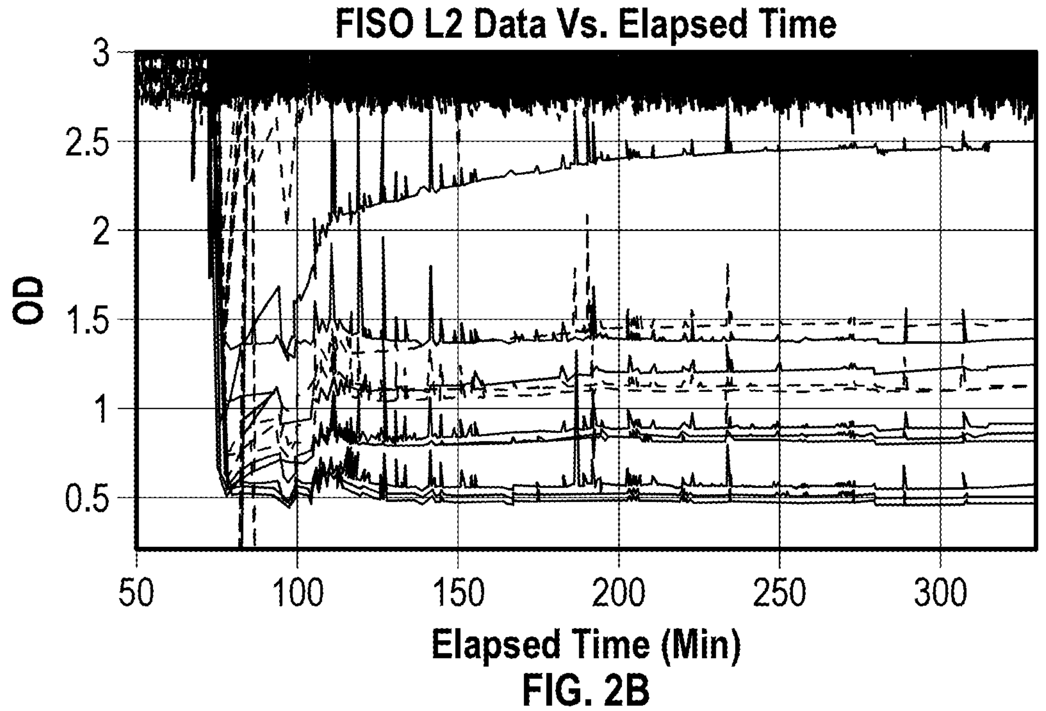
FIG. 2B depicts a graphical representation of optical density spectra of the typical downhole fluids obtained via a guard-line of the focused fluid sampling system over the same elapsed period of time as shown in FIG. 2A, according to one or more embodiments described.

FIG. 2A depicts a graphical representation of optical density spectra of typical downhole fluids obtained via a sample-line of a focused fluid sampling system over an elapsed period of time, according to one or more embodiments. FIG. 2B depicts a graphical representation of optical density spectra of the typical downhole fluids obtained via a guard-line of the focused fluid sampling system over the same elapsed period of time as shown in FIG. 2A, according to one or more embodiments. From the data shown in FIGS. 2A and 2B it can be difficult to determine the relative contamination of the fluid in the sample-line and the guard-line if analyzed in isolation. Additional spectroscopic processing is necessary to unambiguously determine the relative contamination of the fluid in the sample-line with that of the fluid in the guard-line. The additional spectroscopic processing can include analyzing spectral properties such as color absorption, gaseous absorption, dead-oil absorption, and the like, and/or any combination thereof.

Figure 3A:
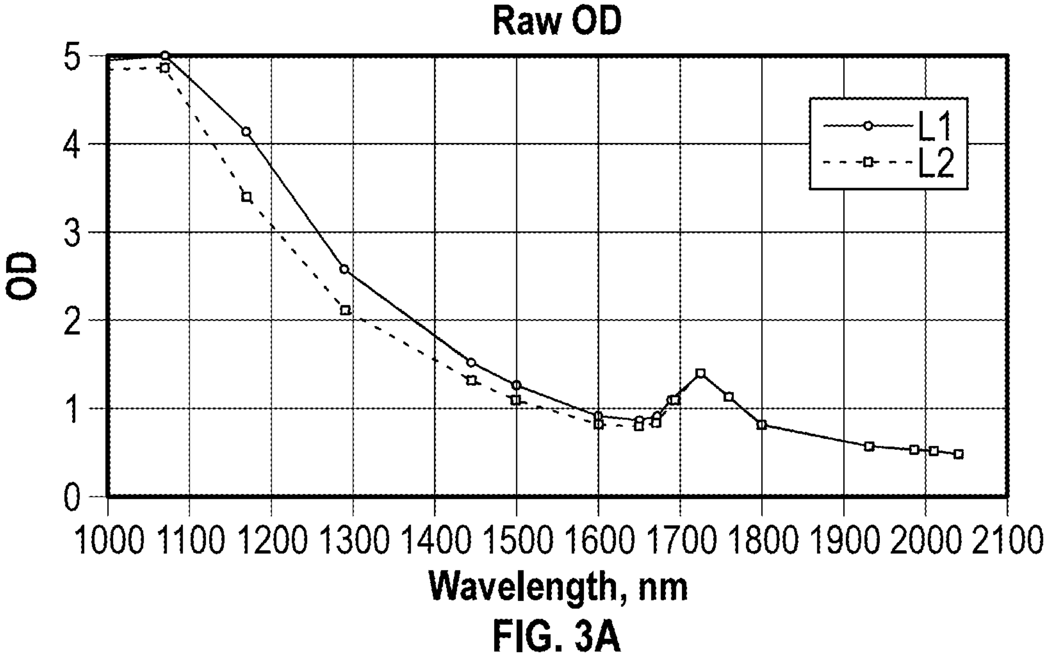
FIG. 3A depicts a graphical representation of a pair of a sample-line and guard-line spectra acquired at the same elapsed time, according to one or more embodiments described.

FIG. 3A depicts a graphical representation of a pair of a sample-line and guard-line spectra acquired at the same elapsed time, according to one or more embodiments. In one or more embodiments, the formation fluid can be dark, and the spectral properties can show a significant amount of color absorption within the color wavelengths. Additionally, the color absorptions in the two flowlines can be noticeably different as depicted in FIG. 3A. While the depiction of gaseous absorption and dead-oil absorption in FIG. 3A can be less clear than the depiction of color absorption in the same, gaseous absorption and dead-oil absorption in the hydrocarbon absorption region can also be distinguished and can be useful information.

Figure 3B:
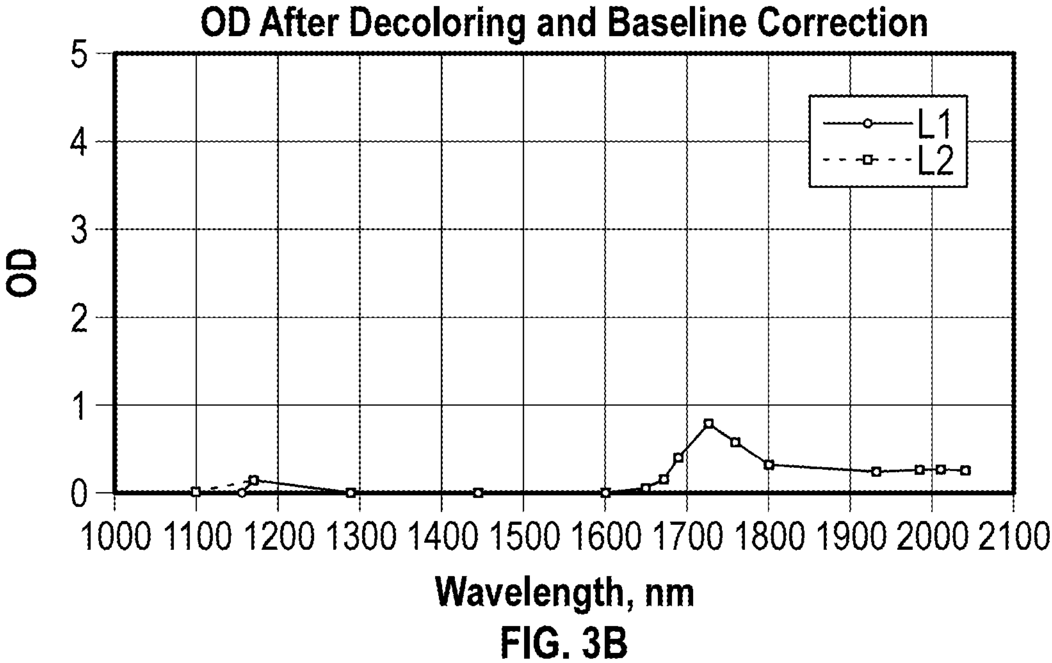
FIG. 3B depicts a graphical representation of the pair of sample-line and guard-line spectra shown in FIG. 3A after decolorizing and normalizing the spectra, according to one or more embodiments described.

FIG. 3B depicts a graphical representation of the pair of sample-line and guard-line spectra shown in FIG. 3A after decolorizing and normalizing the spectra, according to one or more embodiments. In one or more embodiments, one or more pre-processing steps can be carried out. For example, the spectral data in the hydrocarbon absorption region can be decolorized and subsequently all channels can be normalized. In some embodiments, the channels can be normalized at 1,600 nm. In other embodiments, the channels can be normalized at any other suitable wavelength.

The decolorizing of hydrocarbon channels can remove the residual coloration effect expanding into the hydrocarbon channels, whereas the normalization at a certain wavelength, e.g., 1,600 nm, can take out scatterings and the like present in the spectrum. Decolorizing optical density spectra can include removal of absorption caused, dominantly, by asphaltene content, as well as other undesirable colorizing substances. This type of absorption can follow the Urbach tail formalism and can be described by exponential behavior away from the resonance. See, for example, Mullins O. et al., "First observation of the Urbach tail in a multicomponent organic system", Appl. Spectrosc. 46:354-56 (1992), and Mullins O. et al., "Electronic absorption edge of petroleum", Appl. Spectrosc. 46:1405-11 (1992). In one or more embodiments, decolorizing can be achieved by any suitable means that removes unwanted and/or undesirable data caused by or directly linked to color. In some embodiments, the decolorizing can be achieved via the approaches described in Dong, C. et al., "Downhole Measurement of Methane and GOR Content in Formation Fluid Samples," SPEREE (February 2006). In one or more embodiments, normalization can be used to remove undesirable data caused by or directly linked to color. For example, normalization of the spectra with the channel data at 1,600 nm can include subtraction of OD values at the channel 1,600 nm from all spectral data, in which OD at channel 1,600 nm becomes equal to or about zero.

Figure 4A:
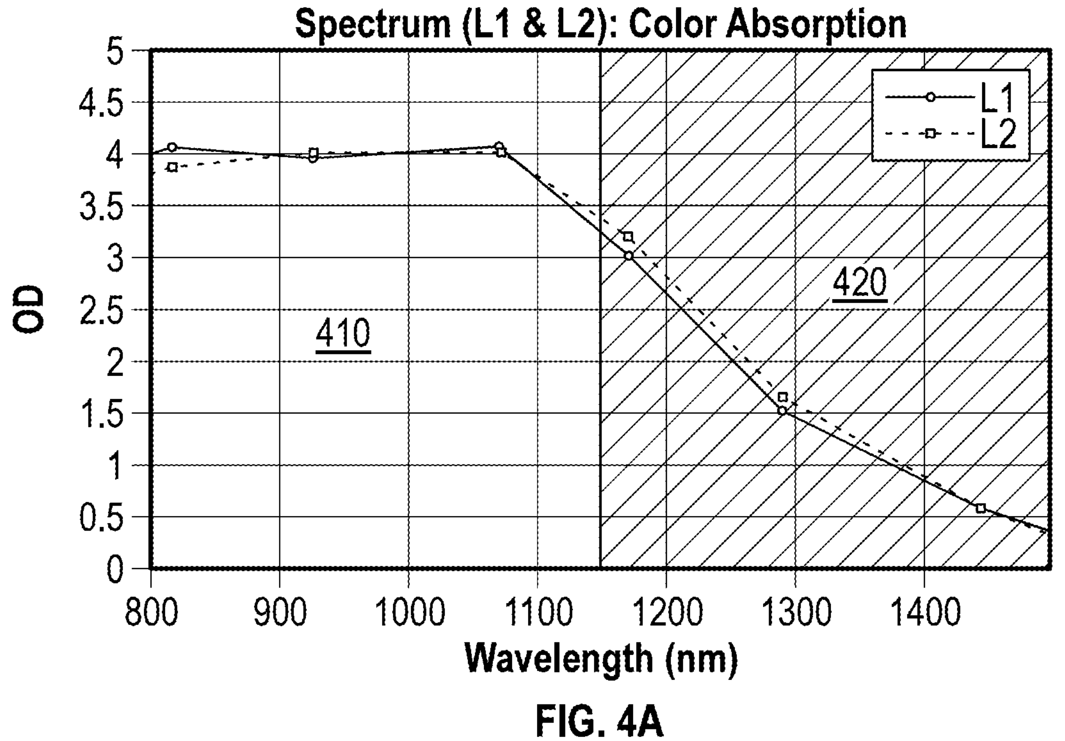
FIG. 4A depicts a graphical representation of a color absorption portion of the spectrum for the sample-line and the guard-line spectra, as shown in FIG. 3B, after preprocessing, according to one or more embodiments described.
Figure 4B:
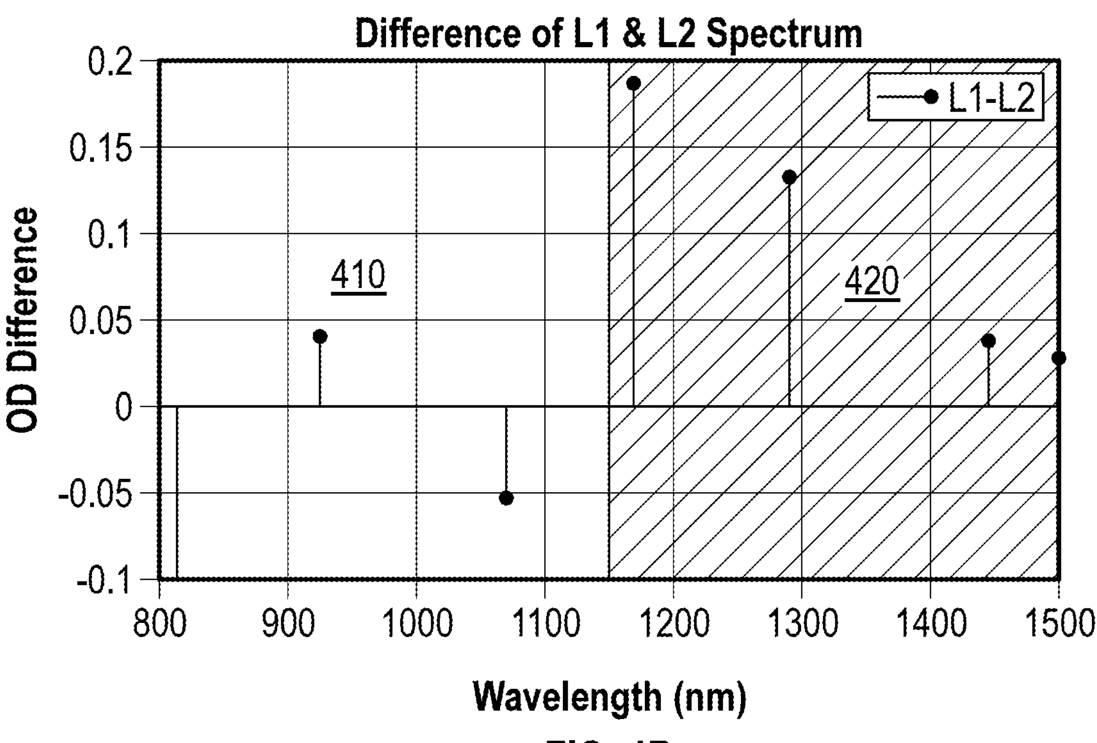
FIG. 4B depicts a graphical representation of an optical density difference between the sample-line and the guard-line spectra, as shown in FIG. 4A, according to one or more embodiments described.

FIG. 4A depicts a graphical representation of a color absorption portion of the spectrum for the sample-line and the guard-line spectra, as shown in FIG. 3B, after preprocessing, according to one or more embodiments. FIG. 4B depicts a graphical representation of an optical density difference between the sample-line and the guard-line spectra, as shown in FIG. 4A, according to one or more embodiments. The OD difference can be computed by subtracting the guard-line OD values from the sample-line OD values (L1-L2). The color channels 410 with the OD values exceeding 3.5 can be considered noisy and discarded if desired. An OD value greater than or equal to 3.5 means the light transmitted through the fluid can be at least around three thousand times less intense than the incident light. The positive OD difference in the remaining color channels 420 can indicate that the fluid in the sample-line is darker than the fluid in the guard-line. The positive OD difference can also mean that the fluid in the sample-line is less contaminated and closer to pure formation fluid in comparison with the fluid in the guard-line. A trend of positive OD differences showing the sample-line is darker and less contaminated can be seen in other color channels, such as 1170 nm, 1290 nm, 1450 nm, 1500 nm, and/or the like.

Figure 5A:
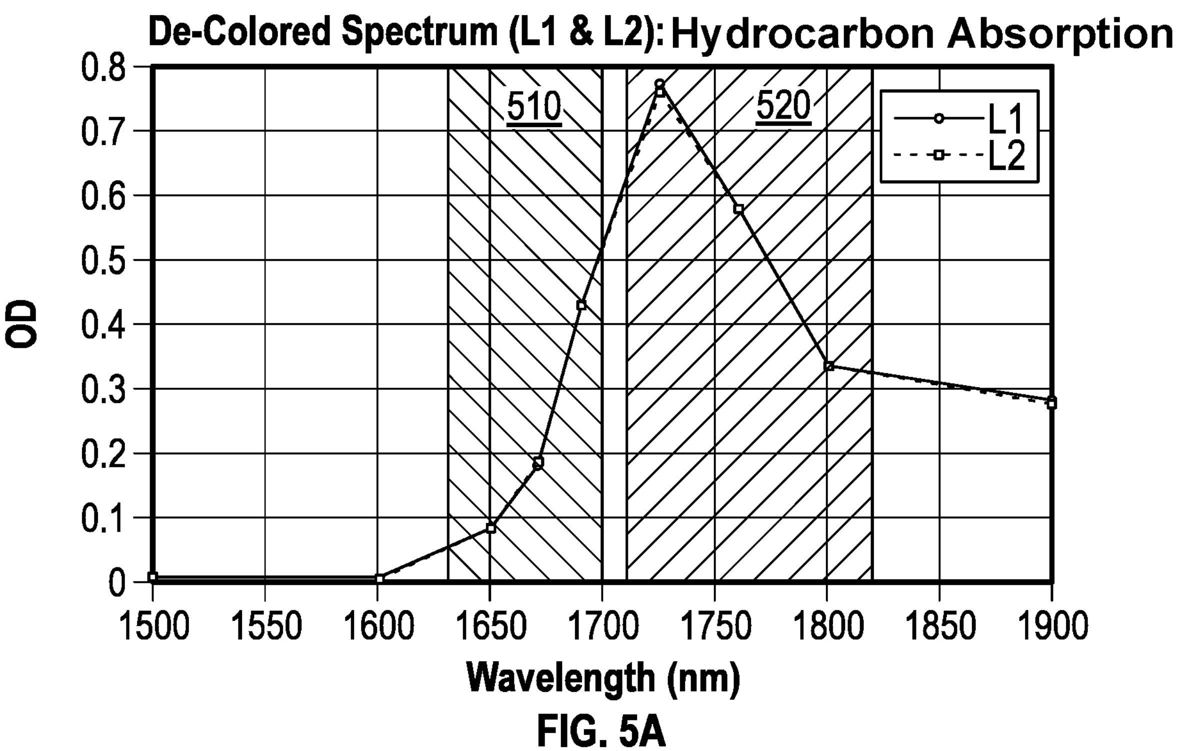
FIG. 5A depicts a graphical representation of a gaseous absorption portion and a dead-oil absorption portion of the pair of a sample-line and guard-line spectra shown in FIG. 3B, after pre-processing, according to one or more embodiments.

FIG. 5A depicts a graphical representation of a gaseous absorption portion and a dead-oil absorption portion of the pair of a sample-line and guard-line spectra shown in FIG. 3B, after pre-processing, according to one or more embodiments. The channels in the gaseous absorption portion 510 can contain wavelength channels in 1650 nm, 1671 nm, 1690 nm, and/or the like, which can be sensitive to a lighter density end (i.e., gaseous) of hydrocarbon fluid. The dead-oil absorption portion 520 which can include the wavelength channels of 1725 nm, 1760 nm, 1800 nm, and/or the like. These wavelength channels in the dead-oil absorption portion can be sensitive to a heavy density end of hydrocarbon fluid. The difference between the sample-line and guard-line can show the relative abundance of the heavy density end of hydrocarbon fluid in two flowlines.

Figure 5B:
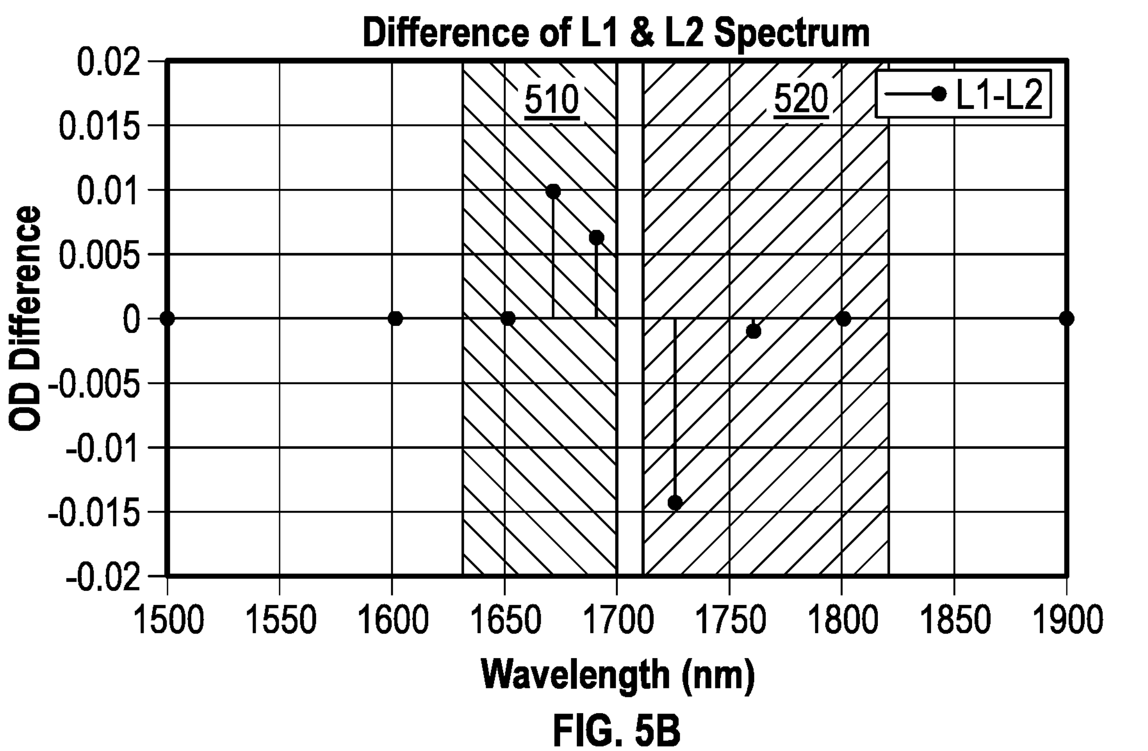
FIG. 5B depicts a graphical representation of an optical density difference between the sample-line and guard-line spectra shown in FIG. 5A.

FIG. 5B depicts a graphical representation of an optical density difference between the sample-line and guard-line spectra shown in FIG. 5A. In one or more embodiments, a positive OD difference can indicate that the fluid in the sample-line contains more light-end components than the fluid in the guard-line. In other words, relative to the guard-line, the fluid in the sample-line can contain less contaminated live fluid, which is consistent with the trend observed in the color absorption spectrum, depicted in FIG. 3A. In one or more embodiments, the wavelength channel at 1,671 nm, which can be referred to as a methane channel, can be useful for this application compared to other hydrocarbons. In one or more embodiments, a negative OD difference can indicate that fluid in the guard-line holds more heavy density end components and, as such, be more contaminated. Ideally, the OD difference in the dead-oil absorption region can show a consistent trend of less contaminated live fluid in the sample-line.

Figures 6A, 6B, 6C:
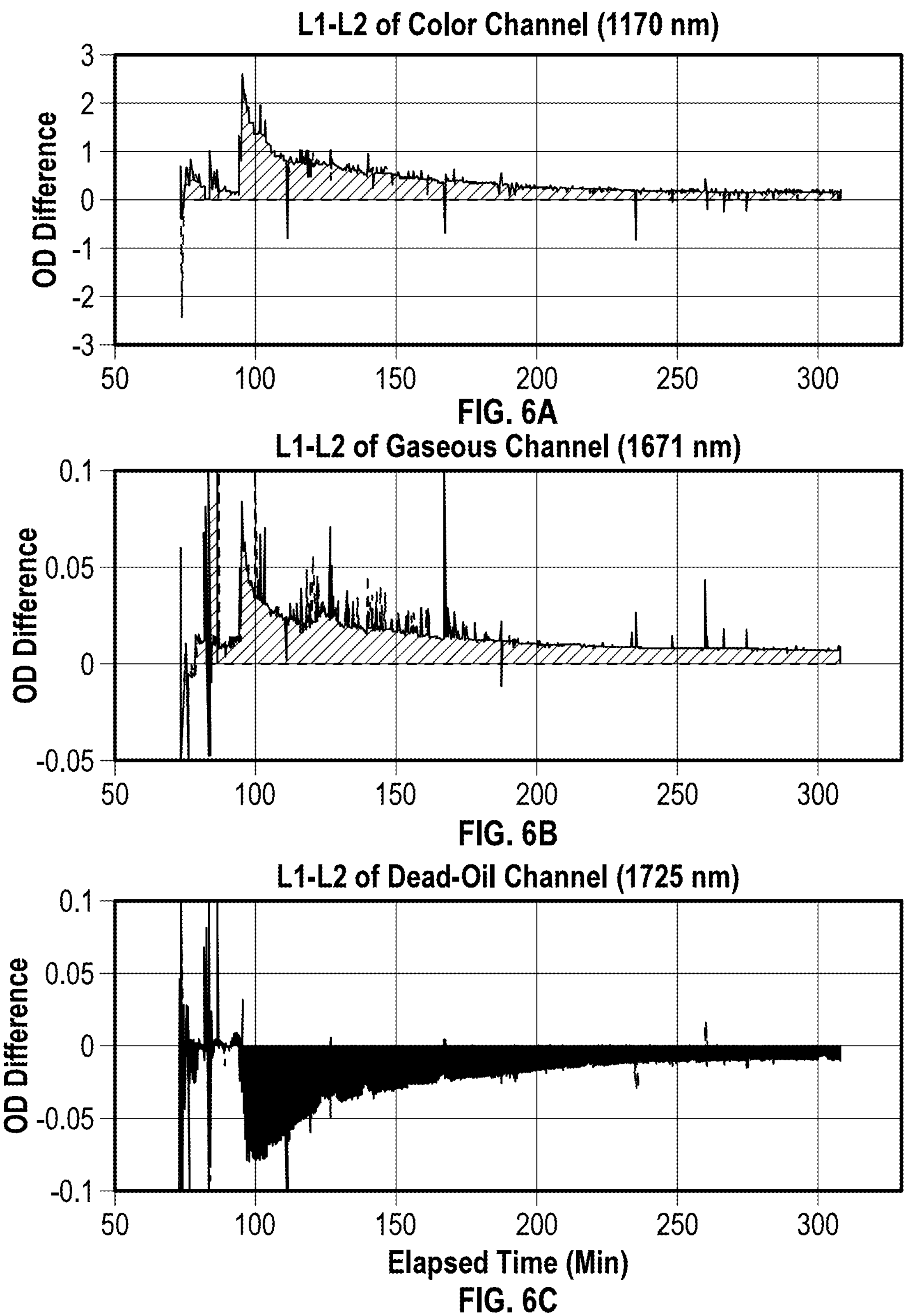
FIG. 6A depicts a graphical representation of an optical density difference plotted versus pumping time of a color channel (1,170 nm) based on the data shown in FIGS. 2A and 2B, according to one or more embodiments described.
FIG. 6B depicts a graphical representation of an optical density difference plotted versus pumping time of a gaseous channel (1,671 nm) based on the data shown in FIGS. 2A and 2B, according to one or more embodiments described.
FIG. 6C depicts a graphical representation of an optical density difference plotted versus pumping time of a dead-oil channel (1,725 nm) based on the data shown in FIGS. 2A and 2B, according to one or more embodiments described.

FIG. 6A depicts a graphical representation of an optical density difference plotted versus pumping time of a color channel (1,170 nm) based on the data shown in FIGS. 2A and 2B, according to one or more embodiments. FIG. 6B depicts a graphical representation of an optical density difference plotted versus pumping time of a gaseous channel (1,671 nm) based on the data shown in FIGS. 2A and 2B, according to one or more embodiments. FIG. 6C depicts a graphical representation of an optical density difference plotted versus pumping time of a dead-oil channel (1,725 nm) based on the data shown in FIGS. 2A and 2B, according to one or more embodiments. In one or more embodiments, the selected channels can be 1170 nm, 1671 nm, 1725 nm, and/or the like, for one or more of color absorption, gaseous absorption, and/or dead-oil absorption. As depicted, consistent trends in the color, gaseous, and dead-oil absorption clearly and unambiguously indicate the fluid in the sample-line was cleaner throughout the entire interval. The progressively decreasing difference in the OD differences denote the difference in composition of the fluids in the two flowlines was decreasing over time.

Figure 7A:
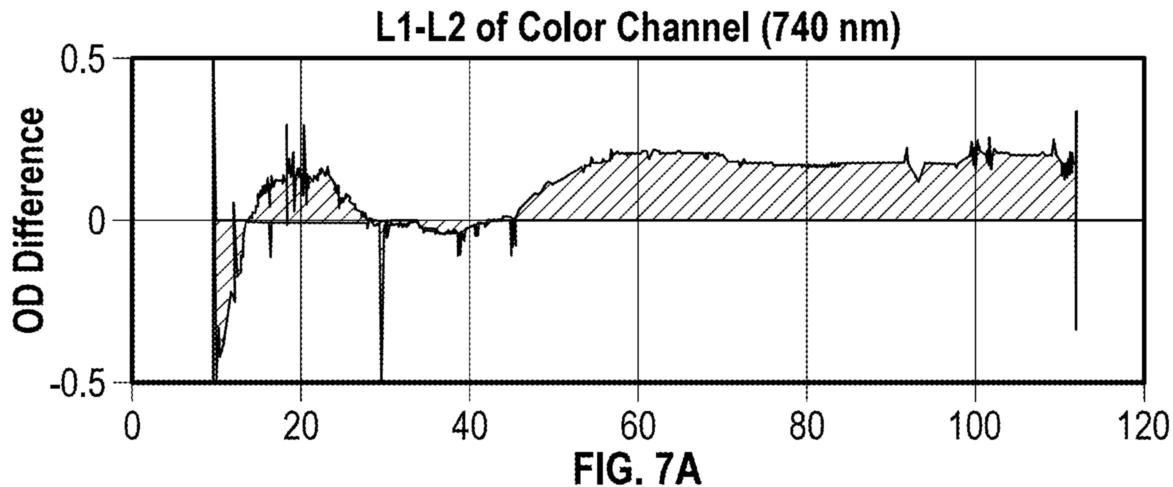
FIG. 7A depicts a graphical representation of an optical density difference plotted versus pumping time of a color channel (1,170 nm) that shows an example of non-stable clean-up behavior, according to one or more embodiments described.
Figure 7B:
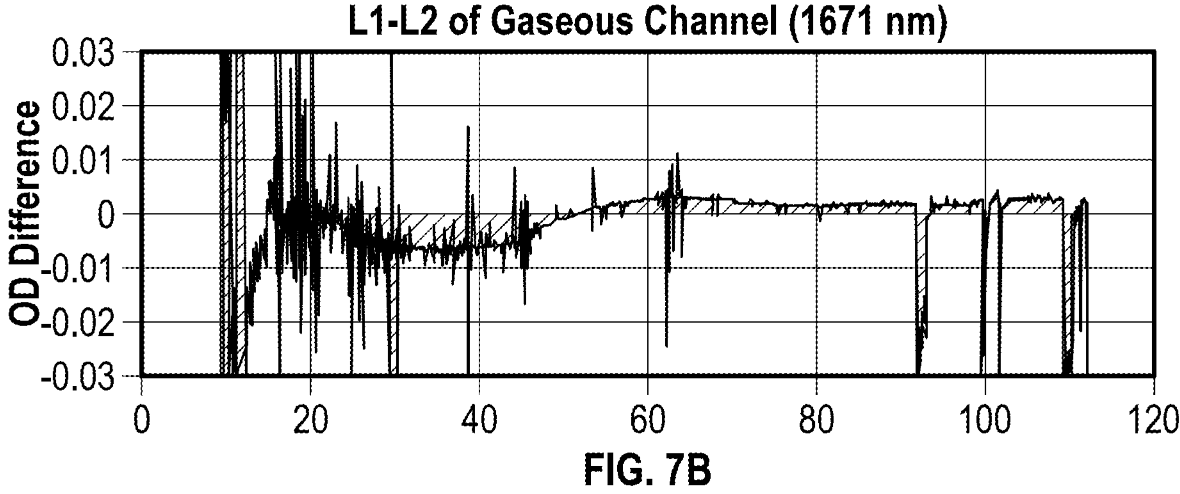
FIG. 7B depicts a graphical representation of an optical density difference plotted versus pumping time of a gaseous channel (1,671 nm) that shows an example of non-stable clean-up behavior, according to one or more embodiments described.
Figure 7C:
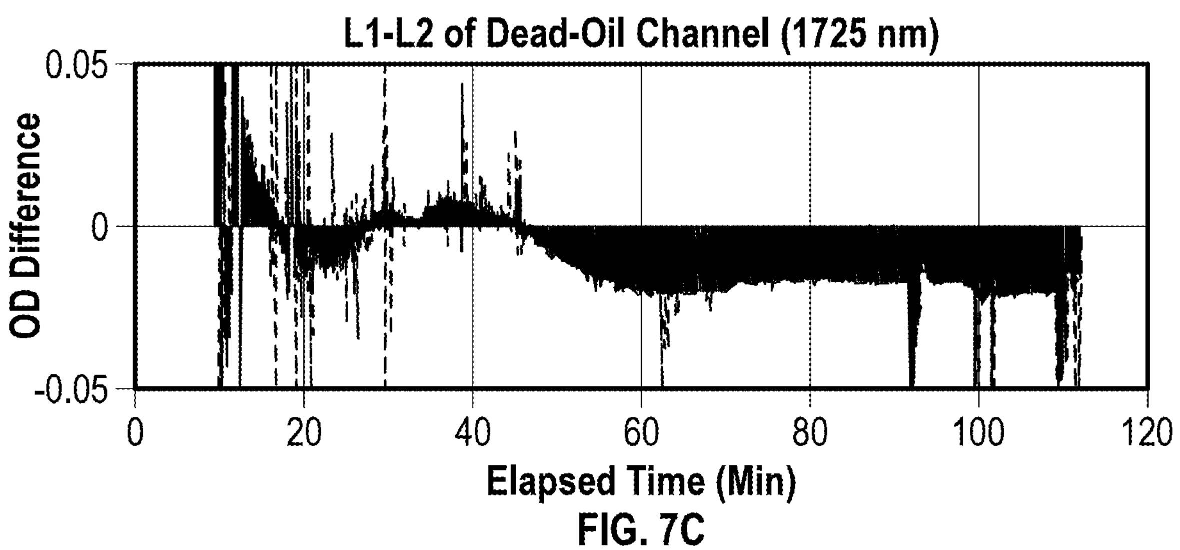
FIG. 7C depicts a graphical representation of an optical density difference plotted versus pumping time of a dead-oil channel (1,725 nm) that shows an example of non-stable clean-up behavior, according to one or more embodiments described.

FIG. 7A depicts a graphical representation of an optical density difference plotted versus pumping time of a color channel (1,170 nm) that shows an example of non-stable clean-up behavior, according to one or more embodiments. FIG. 7B depicts a graphical representation of an optical density difference plotted versus pumping time of a gaseous channel (1,671 nm) that shows an example of non-stable clean-up behavior, according to one or more embodiments. FIG. 7C depicts a graphical representation of an optical density difference plotted versus pumping time of a dead-oil channel (1,725 nm) that shows an example of non-stable clean-up behavior, according to one or more embodiments. As depicted, the selected hydrocarbon fluid was a medium density oil. The selected fluid in the guard-line appears to be cleaner than the sample-line at the beginning of sampling across all three channels. At about 15 minutes, the selected fluid in the sample-line begins showing cleaner fluid. From about 30 to about 45 minutes, the selected fluid in the guard-line begins showing cleaner fluid. After more than about 50 minutes, cleaner fluid in the sample-line persists for the rest of the sampling interval.

Figure 8:
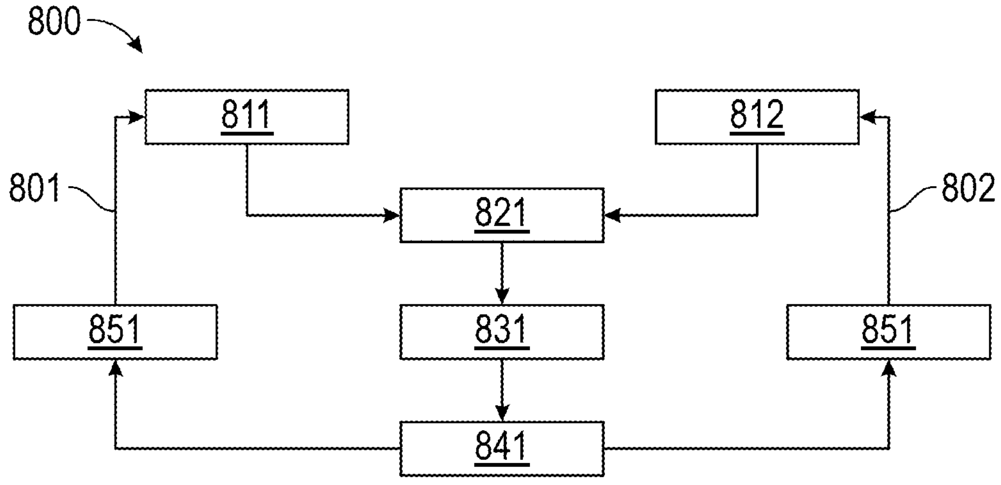
FIG. 8 depicts a process flow diagram of the process, according to one or more embodiments described.

FIG. 8 depicts a process flow diagram 800 of the process, according to one or more embodiments. The process flow diagram 800 shows obtaining a first formation fluid sample using a sample-line of a focused fluid sampling system 801 and obtaining a second formation fluid sample using a guard-line of the focused fluid sampling system 802. Next, the first and second formation fluid samples can be measured by measuring a first optical density spectrum 811 of the first formation fluid sample obtained via the sample-line and measuring a second optical density spectrum 812 of the second formation fluid sample obtained via the guard-line. Next, the first and the second density spectrums 811, 812, respectively, can be decolorized by decolorizing 821 the first and the second optical density spectrums to produce a decolorized first spectrum and a decolorized second spectrum, respectively. Next, the decolorized first spectrum and decolorized second spectrum can be normalized by normalizing 831 the first and the second decolorized spectrums to provide a first normalized spectrum and a second normalized spectrum, respectively. Next, the first normalized spectrum and the second normalized spectrum can be compared by determining a difference 841 between the first and the second normalized spectrums to provide a sampling difference. Next, the process can be repeated 851 from the beginning throughout a given sampling period and/or for as long as may be desired.

In one or more embodiments, the sampling difference can be used to adjust a fluid sampling operation based on the sampling difference. The fluid sampling operation can include quality control, contamination studies, material contents studies, and/or the like, and/or any combination thereof. In some embodiments, a fluid sampling operation can be adjusted or controlled based on the sampling difference. In some embodiments, adjusting the sampling operation can include directing a portion of the first formation fluid sample to a sampling container.

Figure 9:
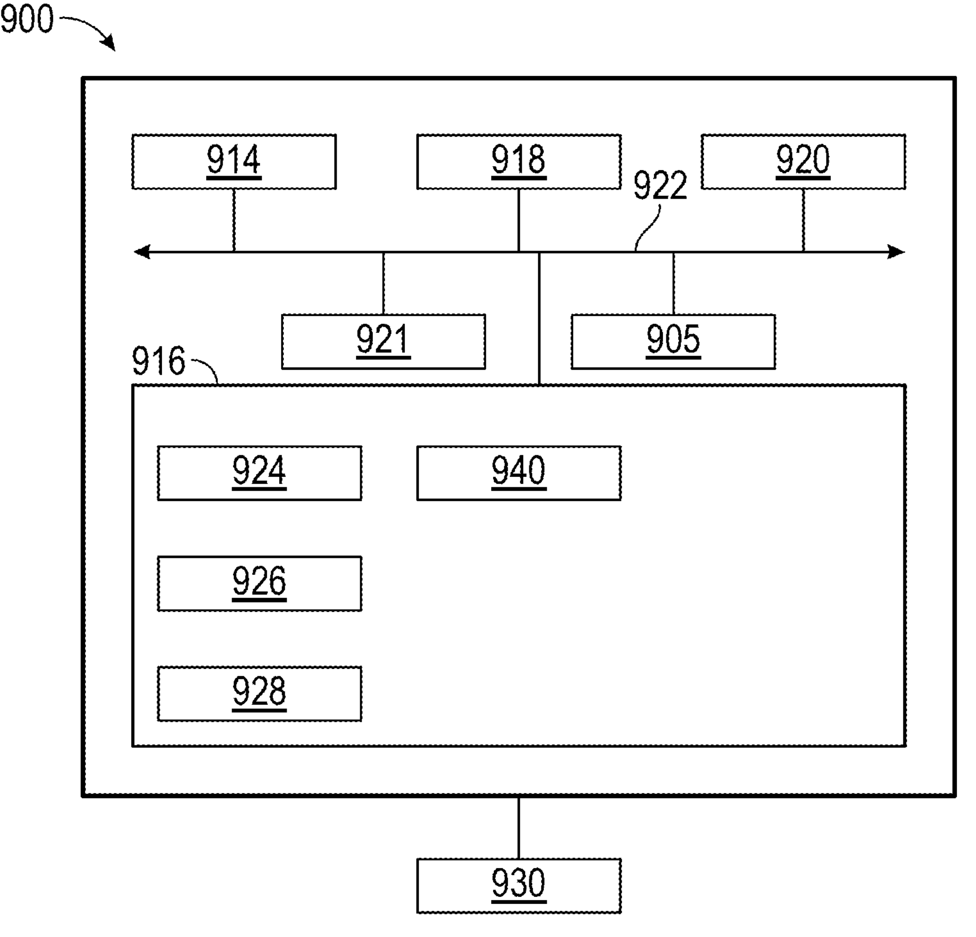
FIG. 9 depicts a schematic of an illustrative computing system that can be configured to carry out one or more steps in the process flow diagram depicted in FIG. 8, according to one or more embodiments described.

FIG. 9 depicts a schematic of an illustrative computing system 900 that can be configured to carry out one or more steps in the process flow diagram depicted in FIG. 8, according to one or more embodiments. The computer system 900 can be located within a facility or can be located elsewhere. One or more chips, for example chips 905 and/or 921, can be or can include field-programmable gate arrays ("FPGAs"), application specific integrated circuits ("ASICs"), chiplets, Multi-Chip-Modules, central processing units ("CPUs"), and/or system-on-chips ("SOCs"), to name a few. The chip can be used in a wide-range of applications, including but not limited to image processing, input data organization, or other digital processing systems. The ASICs can include entire microprocessors, memory blocks including read only memory (ROM), random access memory (RAM), erasable programmable read only memory (EPROM), electrically erasable programmable read only memory (EEPROM), flash memory and other building blocks and can be known as system-on-chip ("SoC").

To achieve its desired functionality, the computing system 900 can include various hardware and software components. Among these components can be one or more processors 914 and a command actuator 940. These hardware components can be interconnected through the use of a number of electrical connections, busses, and/or network connections. In one embodiment, the processor 914, the chip 905, the chip 921, and the command actuator 940 can be communicatively coupled via a bus 922. The bus 922 can be or include any knownn computing system bus. The command actuator 940 can be internal to a data storage device 916.

The chip 905, the chip 921, and/or the command actuator 940 can include, either separately or in some combination, software and hardware, including tangible, non-transitory computer readable medium (not shown), for performing spectroscopy analysis. In some embodiments, the spectroscopy analysis can be interpreted via statistical formulas, such as average mean, median, standard deviation, and the like, or any combination thereof, and/or complex formulas, such as k-means clustering, Otsu's threshold, Fourier's transform, band filters, and the like, or any combination thereof. Other known algorithms and/or suitable algorithms developed in the future can also be used. In some embodiments, the command actuator 940 can be integrated into the chip 905, the chip 921, and/or the processor 914. In some embodiments, the chip 905 and/or the chip 921 can be integrated into the processor 914. Although the command actuator 940 is depicted as being internal to the data storage device 916, in other embodiments, the command actuator 940 can be a peripheral device (not shown) coupled to the computing system 900 or included within a peripheral device (not shown) coupled to the computing system 900.

The command actuator 940 can include instructions that when executed by the command actuator 940 can cause the command actuator 940 to implement at least the functionality of receiving information through a network adapter, processing the information from the one or more fluid samplers through the processor according to the instructions stored in the memory to create a command, and for performing spectroscopy analysis according to the command. In some embodiments, the instructions can, when executed by the command actuator 940, cause the command actuator 940 to use one or more inversion procedures or techniques to perform spectroscopy analysis using the information received. In some embodiments, the instructions can, when executed by the command actuator 940, cause the command actuator 940 to use optimization-based analyses to infer the spectroscopy analysis using the one or more inference models.

In one or more embodiments, the command actuator 940 can work in conjunction with the processor 914 to implement the functionality described above. In some embodiments, the command actuator 940 can execute firmware code stored on the computing system 900, such as on the chip 905, the chip 921, and/or the processor 914. The functionality of the computing system 900 and/or the command actuator 940 can be in accordance with the processes of the present specification described herein. In the course of executing code, the processor 914 and/or the command actuator 940 can receive input from and provide output to a number of the remaining hardware units.

The computing system 900 can be implemented in an electronic device. Examples of electronic devices include servers, desktop computers, laptop computers, cloud-based computers, personal digital assistants ("PDAs"), mobile devices, smartphones, gaming systems, and tablets, among other electronic devices. The computing system 900 can be utilized in any data processing scenario including, standalone hardware, mobile applications, through a computing network, or combinations thereof. Further, the computing system 900 can be used in a computing network, a public cloud network, a private cloud network, a hybrid cloud network, other forms of networks, or combinations thereof. In one example, the processes provided by the computing system 900 can be provided as a service by a third party.

To achieve its desired functionality, the computing system 900 can include various other hardware components. Among these other hardware components can be a number of data storage devices or tangible, non-transitory computer readable medium 916, a number of peripheral device adapters 918, and a number of network adapters 920. These hardware components can be interconnected through the use of a number of electrical connections, busses, and/or network connections.

The chip 905, the chip 921, and/or the processor 914 can include the hardware and/or firmware/software architecture to retrieve executable code from the data storage device 916 and execute the executable code. The executable code can, when executed by the chip 905, the chip 921, and/or the processor 914, cause the chip 905, the chip 921, and/or the processor 914 to implement at least the functionality of receiving information through a network adapter, processing the information from the one or more fluid samplers and performing spectroscopy analysis according to the command.

The data storage device 916 can store data such as executable program code that is executed by the processor 914, the command actuator 940, or other processing devices. The processor 914 can be a central processing unit that is to execute an operating system in the computing system 900. As will be discussed, the data storage device 916 can specifically store computer code representing a number of applications that the processor 914 and/or the command actuator 940 can execute to implement at least the functionality described herein.

In one or more embodiments, the data storage device 916 can include various types of memory modules, including volatile and nonvolatile memory. In one or more embodiments, the data storage device 916 of the present example can include Random Access Memory ("RAM") 924, Read Only Memory ("ROM") 926, and Hard Disk Drive ("HDD") storage 928. Many other types of memory can also be utilized, and the present specification contemplates the use of many varying type(s) of memory in the data storage device 916 as can suit a particular application of the principles described herein. In certain examples, different types of memory in the data storage device 916 can be used for different data storage requirements. In one or more embodiments, in certain examples the processor 914 can boot from Read Only Memory ("ROM") 926, maintain nonvolatile storage in the Hard Disk Drive ("HDD") memory 928, and execute program code stored in Random Access Memory ("RAM") 924. In examples, the chip 905, and the chip 921 can boot from the Read Only Memory ("ROM") 926.

The data storage device 916 can include a computer readable medium, a computer readable storage medium, or a non-transitory computer readable medium, among others. In one or more embodiments, the data storage device 916 can be, an electronic, magnetic, optical, electromagnetic, infrared, or semiconductor system, apparatus, or device, or any suitable combination of the foregoing. More specific examples of the computer readable storage medium can include, for example, the following: an electrical connection having a number of wires, a portable computer diskette, a hard disk, a RAM, a ROM, an EPROM, a Flash memory, a portable compact disc read only memory ("CD-ROM"), an optical storage device, a magnetic storage device, or any suitable combination of the foregoing. In the context of this document, a computer readable storage medium can be any tangible medium that can contain, or store computer usable program code for use by or in connection with an instruction execution system, apparatus, or device. In another example, a computer readable storage medium can be any non-transitory medium that can contain or store a program for use by or in connection with an instruction execution system, apparatus, or device.

The hardware adapters 918, 920 in the computing system 900 can enable the processor 914 to interface with various other hardware elements, external and internal to the computing system 900. In one or more embodiments, the peripheral device adapters 918 can provide an interface to input/output devices, such as, for example, a display device 930, a mouse, and/or a keyboard. The peripheral device adapters 918 can also provide access to other external devices such as an external storage device, a number of network devices such as, for example, servers, switches, and routers, client devices, other types of computing devices, and combinations thereof.

The display device 930 can be provided to allow a user of the computing system 900 to interact with and implement the functionality of the computing system 900. Examples of display devices 930 can include a computer screen, a laptop screen, a mobile device screen, a personal digital assistant ("PDA") screen, and/or a tablet screen, among other display devices 930.

The peripheral device adapters 918 can also create an interface between the processor 914 and the display device 930, a printer, or other media output devices. The network adapter 920 can provide an interface to other computing devices within, for example, a network, thereby enabling the transmission of data between the computing system 900 and other devices located within the network. The network adapter 920 can provide an interface to an external telecommunications network such as a cellular phone network or other radio frequency enabled network, thereby enabling the transmission of data between the computing system 900 and other external devices such as an external storage device, a number of network devices such as, for example, servers, switches, and routers, client servers, radio frequency enabled devices, other client devices, other types of computing devices, and combinations thereof.

The computing system 900 can further include a number of modules used in the implementation of the process and systems described herein. The various modules within the computing system 900 can include executable program code that can be executed separately. In this example, the various modules can be stored as separate computer program products. In another example, the various modules within the computing system 900 can be combined within a number of computer program products; each computer program product including a number of the modules.

While the present disclosure may be susceptible to various modifications and alternative forms, specific embodiments have been shown by way of example in the drawings and have been described in detail herein. However, it should be understood that the present disclosure is not intended to be limited to the particular forms disclosed. Rather, the present disclosure is intended to cover all modifications, equivalents, and alternatives falling within the spirit and scope of the present disclosure as defined by the following appended claims.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim can be not defined above, it should be given the broadest definition persons in the pertinent art have given that term as reflected in at least one printed publication or issued patent. Furthermore, all patents, test procedures, and other documents cited in this application are fully incorporated by reference to the extent such disclosure can be not inconsistent with this application and for all jurisdictions in which such incorporation can be permitted.

While certain preferred embodiments of the present invention have been illustrated and described in detail above, it can be apparent that modifications and adaptations thereof will occur to those having ordinary skill in the art. It should be, therefore, expressly understood that such modifications and adaptations may be devised without departing from the basic scope thereof, and the scope thereof can be determined by the claims that follow.

What is claimed is:

1. A process, comprising:
- obtaining a first formation fluid sample using a sample-line of a focused fluid sampling system;
- obtaining a second formation fluid sample using a guard-line of the focused fluid sampling system;
- measuring a first optical density spectrum of the first formation fluid sample obtained via the sample-line;
- measuring a second optical density spectrum of the second formation fluid sample obtained via the guard-line;
- decolorizing the first optical density spectrum and the second optical density spectrum to produce a decolorized first spectrum and a decolorized second spectrum, respectively;
- normalizing the first decolorized spectrum and the second decolorized spectrum to provide a first normalized spectrum and a second normalized spectrum;
- determining a difference between the first normalized spectrum and the second normalized spectrum to provide a sampling difference; and
- adjusting a fluid sampling operation based on the sampling difference.

2. The process of claim 1, wherein decolorizing the first optical density spectrum and the second optical density spectrum further comprises removing absorption caused by asphaltenes.

3. The process of claim 1, wherein the first normalized spectrum and the second normalized spectrum are normalized at 1600 nm.

4. The process of claim 1, wherein the sampling difference comprises a color absorption portion difference, a gaseous absorption portion difference, and a dead-oil absorption portion difference.

5. The process of claim 1, wherein the focused fluid sampling system comprises a first pump for obtaining the first formation fluid sample using the sample-line and a second pump for obtaining the second formation fluid sample using the guard-line, respectively, and wherein the first pump and the second pump are independently controlled with respect to one another.

6. The process of claim 1, wherein the first formation fluid sample includes native formation fluid and the second formation fluid sample includes contaminated formation fluid.

7. The process of claim 1, wherein the sampling difference includes determining a contamination value.

8. The process of claim 7, wherein adjusting the fluid sampling operation is based on the contamination value.

9. The process of claim 1, wherein adjusting the fluid sampling operation includes directing a portion of the first formation fluid sample to a sampling container.

10. The process of claim 1, wherein normalizing the first decolorized spectrum and the second decolorized spectrum includes Fourier-transform functions.

11. The process of claim 1, wherein determining the difference between the first normalized spectrum and the second normalized spectrum includes subtracting the first normalized spectrum from the second normalized spectrum at a color channel, a gaseous channel, a dead-oil channel, or a combination thereof.

12. The process of claim 1, wherein determining the difference between the first normalized spectrum and the second normalized spectrum includes subtracting the first normalized spectrum from the second normalized spectrum at a plurality of color channels, a plurality of gaseous channels, and a plurality of dead-oil channels.

13. The process of claim 12, wherein any difference of 3.5 or greater in the sampling difference between the first normalized spectrum and the second normalized spectrum at the plurality of color channels is discarded.

14. The process of claim 12, wherein the plurality of color channels comprises a wavelength in a range from 1,000 nm to 1,600 nm, wherein the plurality of gaseous channels comprises a wavelength in a range from greater than 1,600 nm to 1,700 nm, and wherein the plurality of dead-oil channels comprises a wavelength in a range from greater than 1,700 nm to 1,800 nm.

15. The process of claim 1, wherein the first formation fluid sample and the second formation fluid sample are obtained simultaneously with the focused fluid sampling system.

16. The process of claim 1, wherein the first formation fluid sample and the second formation fluid sample are obtained simultaneously with the focused fluid sampling system over a same elapsed period of time.

* * * * *